United States Patent [19]

Stiegmann

[11] Patent Number: 4,735,194
[45] Date of Patent: Apr. 5, 1988

[54] FLEXIBLE ENDOSCOPIC LIGATING INSTRUMENT

[75] Inventor: Greg V. Stiegmann, Denver, Colo.

[73] Assignee: University Patents, Inc., Westport, Conn.

[21] Appl. No.: 3,045

[22] Filed: Jan. 13, 1987

[51] Int. Cl.⁴ .......................... A61B 1/06; A61B 17/12
[52] U.S. Cl. ............................................. 128/6; 128/4; 128/303 A; 128/326
[58] Field of Search ................ 128/4, 6, 326, 303 A, 128/7

[56] References Cited

U.S. PATENT DOCUMENTS

| | | | |
|---|---|---|---|
| 2,704,541 | 3/1955 | Wyatt | 128/4 |
| 3,760,810 | 9/1973 | Van Hoorn | 128/326 |
| 3,870,048 | 3/1975 | Yoon | 128/326 |
| 4,222,380 | 9/1980 | Terayama | 128/4 X |
| 4,257,419 | 3/1981 | Goltner et al. | 128/303 A |
| 4,257,420 | 3/1981 | Terayama | 128/326 X |
| 4,469,483 | 9/1984 | Becker et al. | 604/280 |
| 4,471,766 | 9/1984 | Terayama | 128/6 |

Primary Examiner—William H. Grieb
Attorney, Agent, or Firm—Mathew L. Kalinowski

[57] ABSTRACT

A flexible endoscopic ligating instrument comprises a flexible fiberoptic endoscope on the end of which is secured an outer tube and an inner tube inserted and reciprocally movable within the outer tube. An elastic ring is mounted peripherally on the end of the inner tube which projects beyond the outer tube. A trip wire is fastened to the inner tube to provide rearward motion to the inner tube and thereby cause the elastic ring to slide off and effect ligation. The instrument is particularly suited for ligating lesions deep within the alimentary tract such as esophageal varices.

13 Claims, 1 Drawing Sheet

FLEXIBLE ENDOSCOPIC LIGATING INSTRUMENT

This invention relates to an instrument for ligating lesions in the alimentary tract. More particularly, this invention relates to a flexible endoscopic instrument for ligating mucosal and submucosal lesions deep within the alimentary tract.

Currently, endoscopic treatment of bleeding and potentially bleeding gastrointestinal lesions relies on thermal techniques involving lasers, electrocautery, or a heat probe, or on chemical techniques that include sclerosis. Such techniques for the most part have had limited success with only temporary control of bleeding and a high incidence of complications and rebleeding (Trudeau, W. et. al., Gastrointest. Endosc. Vol. 32, No. 4, pp 264–268, August 1986). It is clear that alternative methods for treatment of such lesions are needed.

Elastic ring ligation of lesions such as hemorrhoids is a widely used and successful technique. Mucosal and submucosal tissue is entrapped by the elastic ligature causing strangulation and sloughing off and eventual fibrosis of the lesion.

Means for effecting ring ligation are well known in the prior art. For example, Van Hoorn, U.S. Pat. No. 3,760,810, discloses an endoscope-equipped instrument for ligation of internal hemorrhoids comprising two rigid tubes capable of relative sliding motion, one inside the other, so as to slide an elastic cord about the structure to be ligated. A pistol-grip member is connected to the two tubes to provide actuated means for moving the tubes. The entire assembly is rigid and is suitable for use within the lower gastrointestinal tract for short distances of not more than about 4–5 cm.

Goltner, U.S. Pat. No. 4,257,419, discloses an instrument for ligating internal hemorrhoids for use in conjunction with a proctoscope. A suction tube which fits inside the proctoscope, provides means for sucking the hemorrhoid into a suction cavity where a ligating ring is applied. Like the Van Hoorn instrument, the Goltner instrument is rigid and its use is confined to lesions that are close to external regions, namely the distal rectum or anus. Neither instrument is suitable for use inside deep body cavities such as the esophagus, stomach, and colon.

A variety of instruments are taught in the prior art that employ laproscope-assisted means for ring ligation of tubular structures. Such instruments are designed primarily for sterilizing the human female or male by tubal ligation. Representative of such instruments are those disclosed by Yoon, U.S. Pat. No. 3,870,048; and Terayayma, U.S. Pat. Nos. 4,257,420 and 4,471,766. All of the disclosed instruments are of size and rigidity suited to open operation. Such size and rigidity preclude their use deep in the alimentary tract.

Accordingly, it is an object of this invention to provide a flexible endoscopic ligating instrument suitable for ligating lesions deep within the alimentary tract.

It is a particular object of this invention to provide an instrument for ligating mucosal and submucosal lesions in the esophagus, stomach, and colon.

It is another object of this invention to provide a novel technique and instrument for effective ligation of lesions deeply seated in the alimentary tract.

It is a further object of this invention to provide a device for applying a ligating ring to a lesion deeply seated within the alimentary tract, which device is attached to a flexible fiberoptic endoscope in a manner to enable the operator to observe and control the entire ligation procedure.

These and other objects will become apparent as description of the invention proceeds.

The ligating instrument according to this invention comprises, in combination, a flexible fiberoptic endoscope, having a forward and a rearward end; an outer tube, having a forward and a rearward end, the rearward end having means for effecting attachment to the forward end of the endoscope; an inner tube, having a forward and a rearward end, and being insertable and reciprocally movable within the outer tube; an elastic ring, peripherally and removably mounted on the forward end of the inner tube, said ring protruding beyond the forward end of the outer tube; and means for imparting said reciprocal motion to the inner tube to cause the ring to slide off and ligate the lesion under treatment.

The flexible endoscope includes, in the convention manner, a fiberoptics illumination source, a fiberoptics visualization mechanism, a biopsy channel, and a suction channel to apply suction to the lesion undergoing treatment.

A variety of means can be employed for fastening the outer tube to the foward end of the endoscope. For example, the outer tube can be of such diameter as to provide a snug friction-fit with the endoscope; the outer tube can be threaded at one end to provide attachment to the threaded end of the endoscope; or a sleeve extending from one end of the outer tube can be snugly fitted over the end of the endoscope to provide secure attachment.

The inner tube possesses an outer diameter such as to provide a close fit when it is inserted within the outer tube, and at the same time, provide easy reciprocal motion within the outer tube.

Both the inner tube and the outer tube can be fabricated of an inert metal such as stainless steel, or of an inert plastic material such as polyethylene, polypropylene, polystyrene, polycarbonate, and the like. Clear plastic material can be advantageously employed to provide an improved field of illumination and vision at the site of operation. The inner surfaces of the tubes can be graduated to provide measure and control of the size of the lesion undergoing ligation. Additionally, the tubes can be made longer or shorter to control the size of the lesion undergoing ligation.

The ligating rings are made of rubber or of an inert plastic compostion. The rings can be impregnated with medication, for example, thrombin or an antibiotic. The rings can also be impregnated with a radio-opaque material such as a barium salt to facilitate visualization by X-rays, or with fine metal particles to permit subsequent thermal treatment induced, for example, by microwave exposure. The rings can be of various colors to aid orientation during multiple lesion treatment.

A fine trip wire is suitable for providing the motion of the inner tube within the outer tube required to fire the ring to effect ligation. The wire can be of flexible braided metal or a monofilament synthetic material. The wire is threaded through the biopsy channel of the endoscope, one end of the wire being attached to a notch in the rearward end of the inner tube, the other end exiting the biopsy channel at the rearward end of the endoscope. It is advantageous to fasten a weighted handle to the exiting end of the wire to provide tension sufficient to prevent premature antegrade motion or slippage of the inner tube. A variety of alternative means can be employed to provide the motion of the inner tube required for firing the ring. For example, an electromagnet incorporated in the outer tube, when activated, could pull the inner tube rearwardly to effect ligation. Simply pressing the inner tube, previously readied with a ligating ring, against the lesion can frequently provide sufficient rearward movement of the inner tube to fire the ring.

The dimensions and flexibility of the inventive instrument are such as to permit ready access to the deeper reaches of the alimentary tract. The overall length can range from about 40 cm to about 200 cm, and the outside diameter from about 6 mm to about 14 mm. Within these approximate ranges, instrument size can be selected that is best suited to the location of the region of operation and the size of the lesion undergoing ligation.

DESCRIPTION OF THE PREFERRED EMBODIMENT

Figure 1:
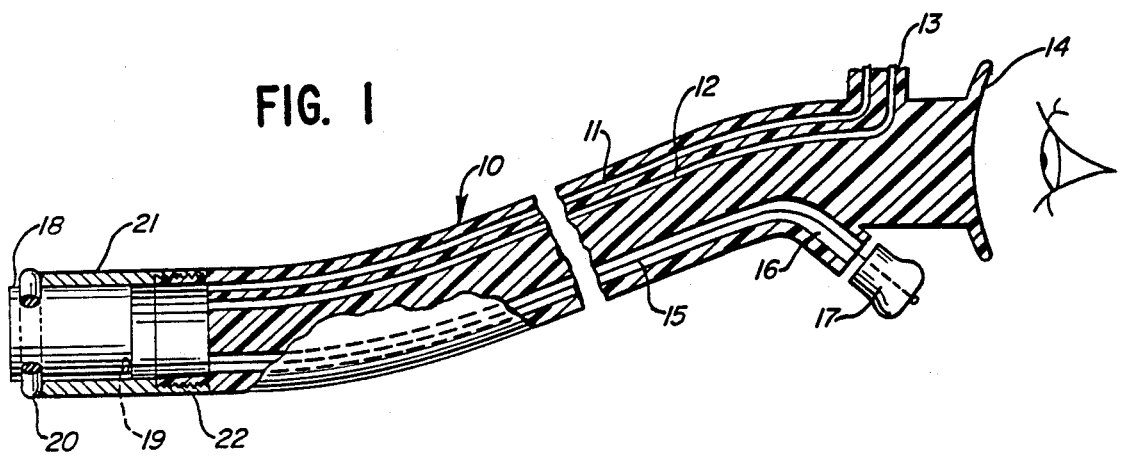
FIG. 1 is a longitudinal view in partial section of the endoscopic ligating instrument in accordance with this invention.

The invention is further illustrated by reference to the drawings wherein like reference numerals designate identical or corresponding parts throughout the several drawings.

FIG. 1 shows flexible endoscope 10 equipped with suction channel 11 and fiberoptics illumination channel 12, both exiting at terminal 13 which is connected to a control box (not shown) for supplying suction and illumination. Eyepiece 14 provides means for viewing the ligation procedure either directly or by video camera and subsequent projection onto a video monitor. Trip wire 15, located in biopsy channel 16, is equipped with weighted handle 17, and is fastened to inner tube 18 at notch 19. Ligating ring 20 is mounted on inner tube 18, which is positioned within outer tube 21. Outer tube 21 is fastened securely to endoscope 10 by means of threaded connection 22.

Figure 2:
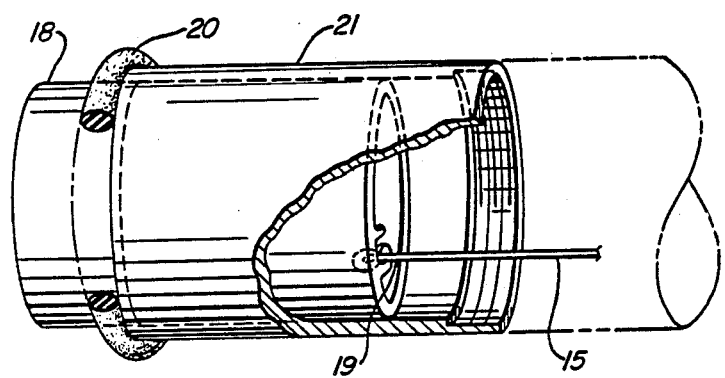
FIG. 2 is a detailed view of the outer tube and the inner tube which are attached to the end of the endoscope.

FIG. 2 illustrates in enlarged detail ligating ring 20 mounted on inner tube 18, which is inserted within outer tube 21. Trip wire 15 is secured to notch 19 which provides for rearward movement of tube 18 required to slide ring 20 around the lesion under treatment.

Figure 3:
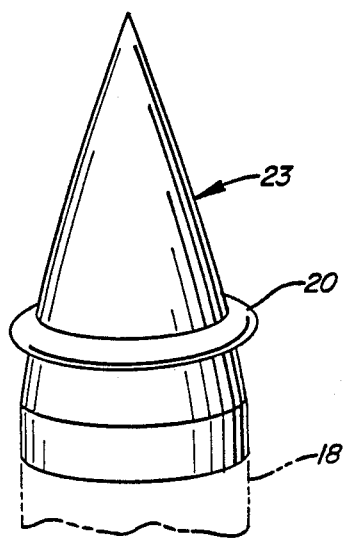
FIG. 3 is a view of an auxiliary device for positioning the ligating ring on the inner tube.

FIG. 3 shows auxiliary device 23 which is used to stretch ring 20 peripherally about tube 18.

In utilization of the instrument, elastic ring 20 is mounted over the forward end of the tube 18 with the aid of device 23. Trip wire 15 exiting via biopsy channel 16 is attached to notch 19 at the rearward end of tube 18, and the assembly is placed inside tube 21, which had been securely attached to endoscope 10. Tube 18 is seated within tube 21 with ring 20 protruding just beyond the end of tube 21, as shown in FIG. 1 and FIG. 2. Trip wire 15 exiting at the rearward end of endoscope 10 is held in tension by weighted handle 17.

After placement of an endoscopic overtube in the patient, the instrument is introduced into the alimentary tract. The target lesion is visualized and the instrument is advanced under direct vision until tube 18 surrounds the intended target. Once full 360° contact is made, suction is activated drawing the lesion into tube 18. When the lesion is totally within tube 18, as witnessed by complete red-out, trip wire 15 is pulled, ring 20 slides off and becomes securely fixed around the base of the target lesion.

Multiple lesions require removal and reinsertion of the instrument with an individual loading of a ring for each lesion. The overtube facilitates multiple ligations and prevents inadvertent firing of the ring during passage through the oropharynx.

Results obtained by utilization of the inventive instrument are presented in the following examples.

EXAMPLE 1

This example evaluates the use of the instrument in a dog esophageal varices model.

MATERIALS AND METHODS.

Esophageal varices were produced in ten 30–40 kg dogs using caval portal shints and ameroid constrictors. Four to ten months later, 37 variceal sites were ligated. The animals were sacrificed 1–69 days later and the treated areas were histologically examined.

RESULTS

Varices from 2–5 mm indiameter were produced in the dogs. Endoscopic ligation was successful on first attempt in 34 of 37 sites. Histologically, at 24 hours, treated sites had ischemic necrosis of mucosa and submucosa; underlying muscularis was intact. Acute inflammatory reaction was present at day 1 at demarcation of viable and necrotic tissue. Granulation tissue appeared by day 3 and sloughing necrotic tissue by day 4. Full thickness replacement of mucosa and submucosa with maturing scar tissue was present at days 5–30. Re-epithelialization was complete by days 14–19. Inflammation and scarring obliterated mucosa and submucosa, but left muscularis propria intact at treated sites. No adverse clinical sequelae were observed.

It is concluded that ligation of varices with the inventive instrument results in obliteration of vascular channels in the mucosa and submucosa by a process of inflammation and scar formation.

EXAMPLE 2

This example evaluates clinical experience with the inventive instrument for treatment of esophageal varices.

MATERIAL AND METHODS

Nineteen patients with esophageal varices were treated. Six were actively bleeding and 11 had ceased bleeding at initial treatment. Five had undergone and failed sclerotherapy. Varices were graded endoscopically on a scale of I–IV. Effect of treatment were accessed by number and size of varices remaining at repeat endoscopy and number of bleeding episodes following initiation of treatment. Initial treatments consisted of 2–5 variceal ligations at GE junctions and distal 10 cm of the esophagus. Re-endoscopy and re-treatment were done at intervals of 4–14 days. A total of 195 ligations were performed during 57 sessions. Follow-up ranged from 30–120 days.

RESULTS

Ten patients had grade IV, 7 grade III, and 2 grade II varices at first treatment. Two to 5 varies were present in each patient (mean 3.6) Repeat endoscopy showed progressive diminution in number and size in varices at each subsequent session. Shallow 1–1.5 cm ulcers were consistently observed following slough of the ligated sites at 4–10 days. Four patients achieved complete variceal obliteration after 4 and 5 treatment sessions. One self-limited (three unit) bleed occurred two weeks following treatment but prior to variceal obliteration. One self-limited secondary hemorrhage occurred four days after initial treatment. Perforation or other complications were not observed.

It is concluded from this clinical experience that treatment of esophageal varices with the instrument of this invention is safe, well tolerated, and effective in controlling hemorrhage and obliterating varices.

Furthermore, it is clear from the above-described examples and results that the instrument of this invention provides a novel and successful technique for ligation of lesions within the alimentary tract. The instrument can be employed to particular advantage in per oral ligation of lesions deeply seated in the alimentary tract.

Although this invention has been described with particular reference to certain preferred embodiments thereof, it is understood that variations and modifications can be effected within the scope and spirit of the appended claims. It is intended that all material contained in the above description, figures, and examples be interpreted in an illustrative and not limiting sense.

What is claimed is:

1. A flexible endoscopic instrument for ligating lesions deep within the alimentary tract, which instrument comprises, in combination:
   (a) a flexible fiberoptic endoscope having a forward end and rearward end, said endoscope including illumination and viewing means, suction-providing means, and a biopsy channel;
   (b) an outer tube having a forward end and a rearward end, the rearward end having means for providing attachment to the forward end of the endoscope;
   (c) an inner tube having a forward end and rearward end, and being insertable and reciprocally slidable within the outer tube;
   (d) an elastic ring peripherally and removably stretched on the forward end of the inner tube; and
   (e) means for imparting said reciprocal sliding motion to the inner tube to cause the elastic ring to slide off and effect ligation of the lesion.

2. A flexible endoscopic instrument for ligating lesions deep within the alimentary tract, which instrument comprises, in combination:
   (a) a flexible fiberoptic endoscope having a forward end and a rearward end, said endoscope including illumination and viewing means, suction-providing means, and a biopsy channel;
   (b) an outer tube having a forward end and a rearward end, the rearward end having means for providing attachment to the forward end of the endoscope;
   (c) an inner tube having a forward end and a rearward end, and being insertable and reciprocally slidable within the outer tube;
   (d) an elastic ring peripherally and removable stretched on the forward end of the inner tube; and
   (e) means for imparting said reciprocal sliding motion to the inner tube to cause the elastic ring to slide off and effect ligation of the lesion, said means comprising a flexible wire threaded through the biopsy channel one end of the wire being attached to the rearward end of the inner tube, the other end of the wire exiting the biopsy channel at the rearward end of the endoscope, said exiting end of the wire having handle means attached thereto.

3. The instrument of claim 2 wherein the illumination and viewing means include optical fibers, disposed within the endoscope, for transmitting light beams produced by a source outside the endoscope.

4. The instrument of claim 2 wherein the suction-providing means includes a channel disposed within the endoscope, the rearward end of the channel being attached to a source of suction and the forward end of the channel being in communication with the interior hollow space encompassed by the inner and outer tubes.

5. The instrument of claim 2 wherein the forward end of the endoscope and the rearward end of the outer tube are threaded to provide means for secure attachment of one to the other.

6. The instrument of claim 2 wherein the inner and outer tubes are made of transparent material.

7. The instrument of claim 2 wherein the inner surfaces of the inner and outer tubes are graduated.

8. The instrument of claim 2 wherein the elastic ring is impregnated with medication.

9. The instrument of claim 14 wherein the elastic ring is impregnated wiht finely divided metal particles.

10. The instrument of claim 14 wherein the elastic ring is impregnated with a radio-opaque substance.

11. The instrument of claim 14 wherein the length and flexibility are sufficient to provide access to the far reaches of the alimentary tract.

12. A method of ligating lesions in a region of the alimentary tract which comprises:
   (a) providing a flexible endoscopic instrument having a releasable ligating ring attached thereto;
   (b) inserting the instrument into the alimentary tract to the lesion site;
   (c) abutting the lesion site with the forward end of the instrument;
   (d) providing a means for drawing the lesion into the instrument;
   (e) drawing the lesion into the instrument for a distance; and
   (f) releasing the ligating ring from the instrument to effect the ligation.

13. The method of claim 12 wherein the region of the alimentary tract includes the esophagus.

* * * * *

(12) REEXAMINATION CERTIFICATE (4335th)
United States Patent
Stiegmann

(10) Number: US 4,735,194 C1
(45) Certificate Issued: May 8, 2001

(54) FLEXIBLE ENDOSCOPIC LIGATING INSTRUMENT

(75) Inventor: Greg V. Stiegmann, Denver, CO (US)

(73) Assignee: The United States of America as represented by the Department of Veterans Affairs, Washington, DC (US)

Reexamination Request:
No. 90/005,573, Nov. 23, 1999

Reexamination Certificate for:
Patent No.: 4,735,194
Issued: Apr. 5, 1988
Appl. No.: 07/003,045
Filed: Jan. 13, 1987

(51) Int. Cl.$^7$ ............................... A61B 1/06; A61B 17/12
(52) U.S. Cl. ........................ 600/104; 600/127; 600/117; 606/140
(58) Field of Search .................................. 606/139, 140, 606/141, 144; 600/104, 106, 127

(56) References Cited

PUBLICATIONS

Encoskopische Blutsillung durch Gummiring–Strangulation, Munchener Medisinische Wochenschirift 118:97–98 (1976).*

* cited by examiner

*Primary Examiner*—John P. Leubecker

(57) ABSTRACT

A flexible endoscopic ligating instrument comprises a flexible fiberoptic endoscope on the end of which is secured an outer tube and an inner tube inserted and reciprocally movable within the outer tube. An elastic ring is mounted peripherally on the end of the inner tube which projects beyond the outer tube. A trip wire is fastened to the inner tube to provide rearward motion to the inner tube and thereby cause the elastic ring to slide off and effect ligation. The instrument is particularly suited for ligating lesions deep within the alimentary tract such as esophageal varices.

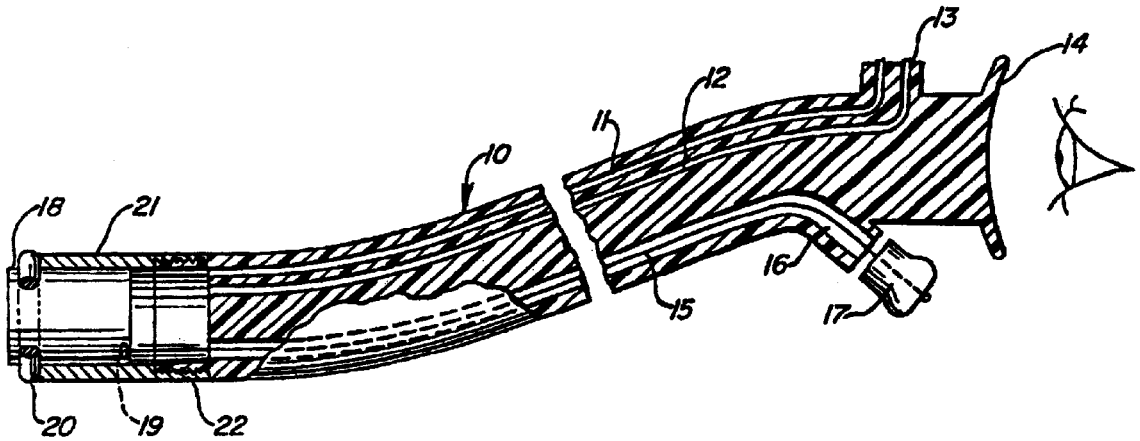

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2–8 is confirmed.

Claim 11 is cancelled.

Claims 1, 9, 10 and 12 are determined to be patentable as amended.

Claim 13, dependent on an amended claim, is determined to be patentable.

New Claims 14–16 are added and determined to be patentable.

1. A flexible endoscopic instrument for ligating lesions deep within the alimentary tract, which instrument comprises, in combination:
   (a) a flexible fiberoptic endoscope having a forward end and a rearward end, said endoscope including illumination and viewing means, suction-providing means, and biopsy channel;
   (b) an outer tube having a forward end and a rearward end, the rearward end having means for providing attachment to the forward end of the endoscope;
   (c) an inner tube having a forward end and a rearward end, and being insertable and reciprocally slidable within outer tube;
   (d) an elastic ring peripherally and removably stretched on the forward end of the inner tube; and
   (e) *triggering* means *in said biopsy channel and extending from said inner tube to the rearward end of said endoscope* for [imparting said reciprocal sliding motion to the inner tube to cause the elastic ring to slide off] *removably releasing said elastic ring and allowing said ring to slide off said inner tube* and effect ligation of the lesion.

9. The instrument of claim [14] *1* wherein the elastic ring is impregnated [wiht] *with* finely divided metal particles.

10. The instrument of claim [14] *1* wherein the elastic ring is impregnated with a radio-opaque substance.

12. A method of ligating lesions in a region of the alimentary tract which comprises:
   (a) providing a flexible endoscopic instrument having a releasable ligating ring attached thereto, *said instrument having a biopsy channel through which a triggering means for releasing said ring extends*;
   (b) inserting the instrument into the alimentary tract to the lesion site;
   (c) abutting the lesion site with the forward end of the instrument;
   (d) providing a means for drawing the lesion into the instrument;
   (e) drawing the lesion into the instrument for a distance [and]
   (f) *triggering said triggering means; and*
   (g) releasing the ligating ring from the instrument to effect the ligation.

*14. A method according to claim 12 wherein said triggering means is a trip wire and wherein triggering is accomplished by pulling the trip wire to release the ring.*

*15. A flexible endoscope instrument according to claim 1 wherein said triggering means is a trip wire which upon pulling allows said ring to slide off said inner tube and effect ligation of the lesion.*

*16. The instrument of claim 1 wherein the length and flexibility of said flexible endoscopic instrument is sufficient to provide access to the far reaches of the alimentary tract.*

* * * * *